US00PP24614P3

(12) United States Plant Patent
Schäfer

(10) Patent No.: US PP24,614 P3
(45) Date of Patent: Jul. 8, 2014

(54) VARIETY OF BASIL PLANT NAMED 'WILD MAGIC'

(50) Latin Name: *Ocimum basilicum*
Varietal Denomination: Wild Magic

(75) Inventor: Udo Schäfer, Wolsier (DE)

(73) Assignee: Herbalea GmbH, Grolsheim (DE)

( * ) Notice: Subject to any disclaimer, the term of this patent is extended or adjusted under 35 U.S.C. 154(b) by 121 days.

(21) Appl. No.: 13/385,805

(22) Filed: Mar. 7, 2012

(65) Prior Publication Data

US 2013/0239271 P1 Sep. 12, 2013

(51) Int. Cl.
*A01H 5/00* (2006.01)
*A01H 5/02* (2006.01)

(52) U.S. Cl.
CPC ..... *A01H 5/02* (2013.01)
USPC ..... Plt./258

(58) Field of Classification Search
CPC ..... A01G 31/06; C07C 67/08
USPC ..... Plt./258
See application file for complete search history.

(56) References Cited

U.S. PATENT DOCUMENTS

PP13,486 P2 * 1/2003 Bowden et al. ..... Plt./258
PP16,260 P2 * 2/2006 Bennerup ..... Plt./258

OTHER PUBLICATIONS

UPOV PLUTO QZ PBR Application Publication for 'Wild Magic' Feb. 15, 2011.*

* cited by examiner

*Primary Examiner* — Wendy C Haas
(74) *Attorney, Agent, or Firm* — The Webb Law Firm

(57) ABSTRACT

'Wild Magic' is a new variety of basil plant having tolerance to low temperatures, numerous flowers, and leaves with dark violet colored and prominent veins.

11 Drawing Sheets

Botanical classification: *Ocimum basilicum.*
Varietal denomination: 'WILD MAGIC'.

BACKGROUND OF THE NEW PLANT

The present invention comprises a new and distinct cultivar of basil plant, botanically known as *Ocimum basilicum* and hereinafter referred to by the cultivar name 'Wild Magic'.

The new variety was discovered and selected by the breeder in a cultivated environment in July of 2009 in Wolsier, Germany (located in the region of Brandenburg) as a naturally occurring open-pollinated new variety in a population of unpatented and unnamed *Ocimum basilicum* plants. Subsequently, the new variety was asexually reproduced by cuttings in Wolsier, Germany in 2010. Further asexual reproductions at the same location has demonstrated that the combination of characteristics as herein disclosed for the new cultivar are retained and reproduced true to type through successive generations of asexual reproduction.

The following observations, measurements and comparisons describe 8-week-old plants grown in an open field with full sun, watered as needed, and receiving weekly fertilization treatments accented with nitrogen in Wolsier, Germany. The plants were exposed to daytime temperatures of 20-30° C., and evening temperatures of 10-20° C. Color observations were taken under natural light, and the color references are made to The R.H.S. Colour Chart of The Royal Horticulture Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'Wild Magic' which, in combination, distinguish this basil plant as a new and distinct cultivar:

1. Tall and well-branched plant habit;
2. Aromatic-spicy fragrance;
3. Condiment-like taste;
4. Tolerant to Fusarium, Botrytis, and Pythium; and
5. Low temperature tolerance.

Further, the new variety exhibits a tall and well-branched habit like basil variety 'Ajaka' (U.S. Plant patent application Ser. No. 13/385,808). However, 'Wild Magic' has very dark violet leaves and an aromatic-spicy fragrance, while 'Ajaka' has green leaves and a sweet-spicy fragrance. The following Table 1 provides a further comparative listing of botanical characteristics of 'Wild Magic' and 'Ajaka'.

TABLE 1

| Botanical characteristics | 'Wild Magic' | 'Ajaka' |
|---|---|---|
| Leaf length: | 6 cm. | 5 cm. |
| Number of flowers per plant: | About 800 | About 150 |
| Flower longevity: | 6-8 weeks | 4-6 weeks |

BRIEF DESCRIPTION OF THE DRAWINGS

The accompanying photographic drawings illustrate the new variety, with the colors being as nearly true as is possible with color illustrations of this type.

DESCRIPTION OF THE PLANT

Figure 1:
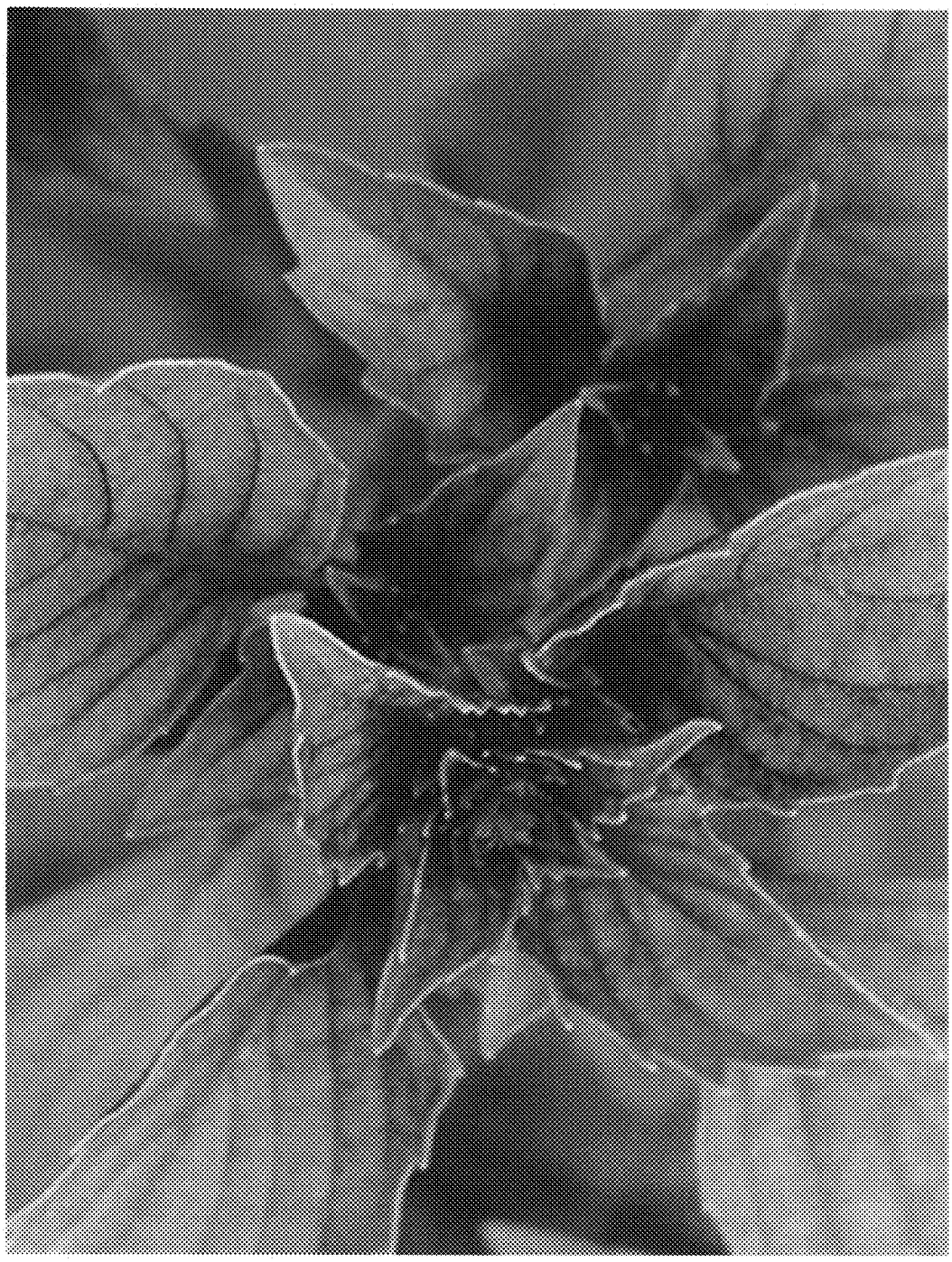
FIG. 1 is a close-up photograph of the leaves of the new variety.
Figure 2:
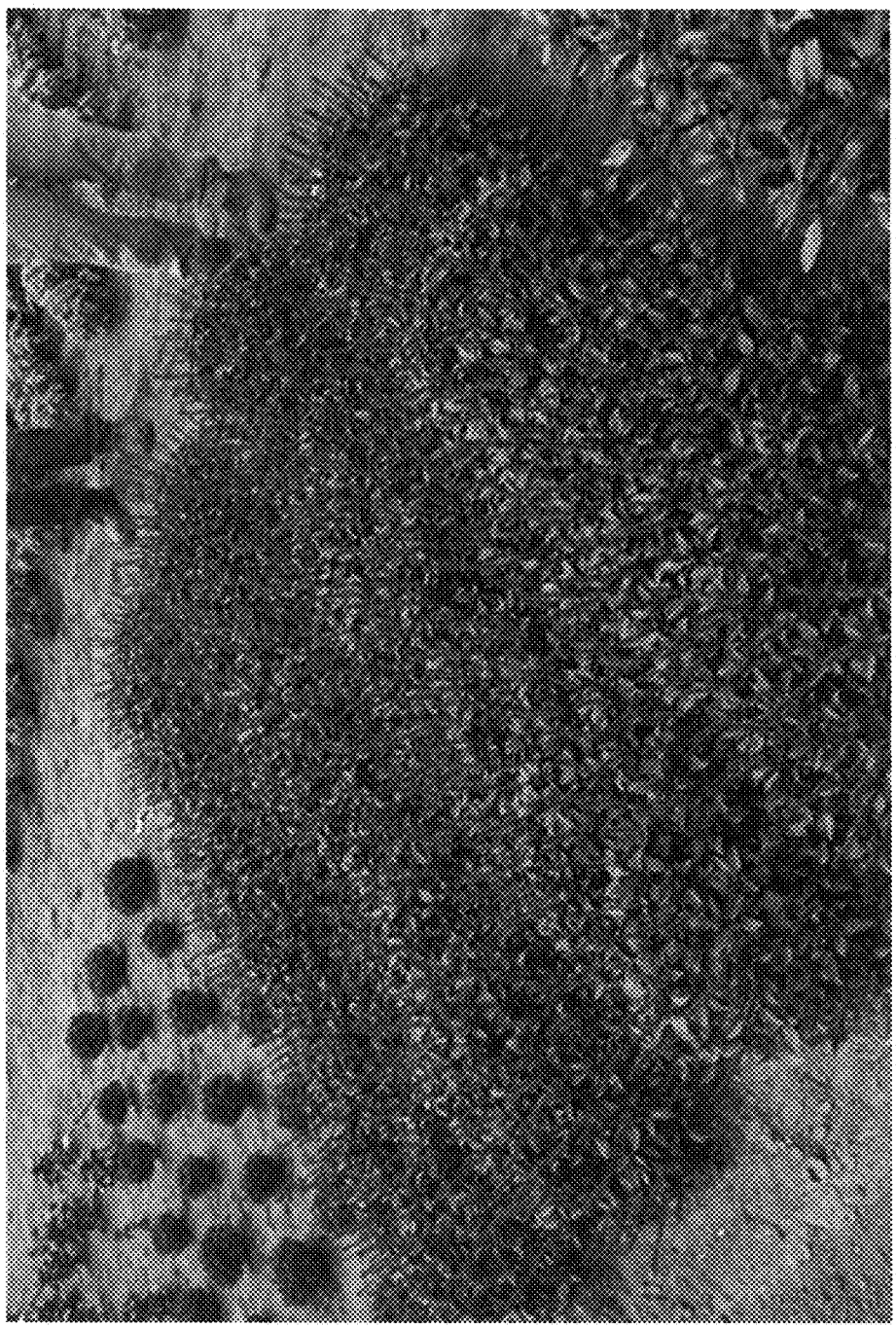
FIG. 2 is a photograph of a field of plants of the new variety.
Figure 3:
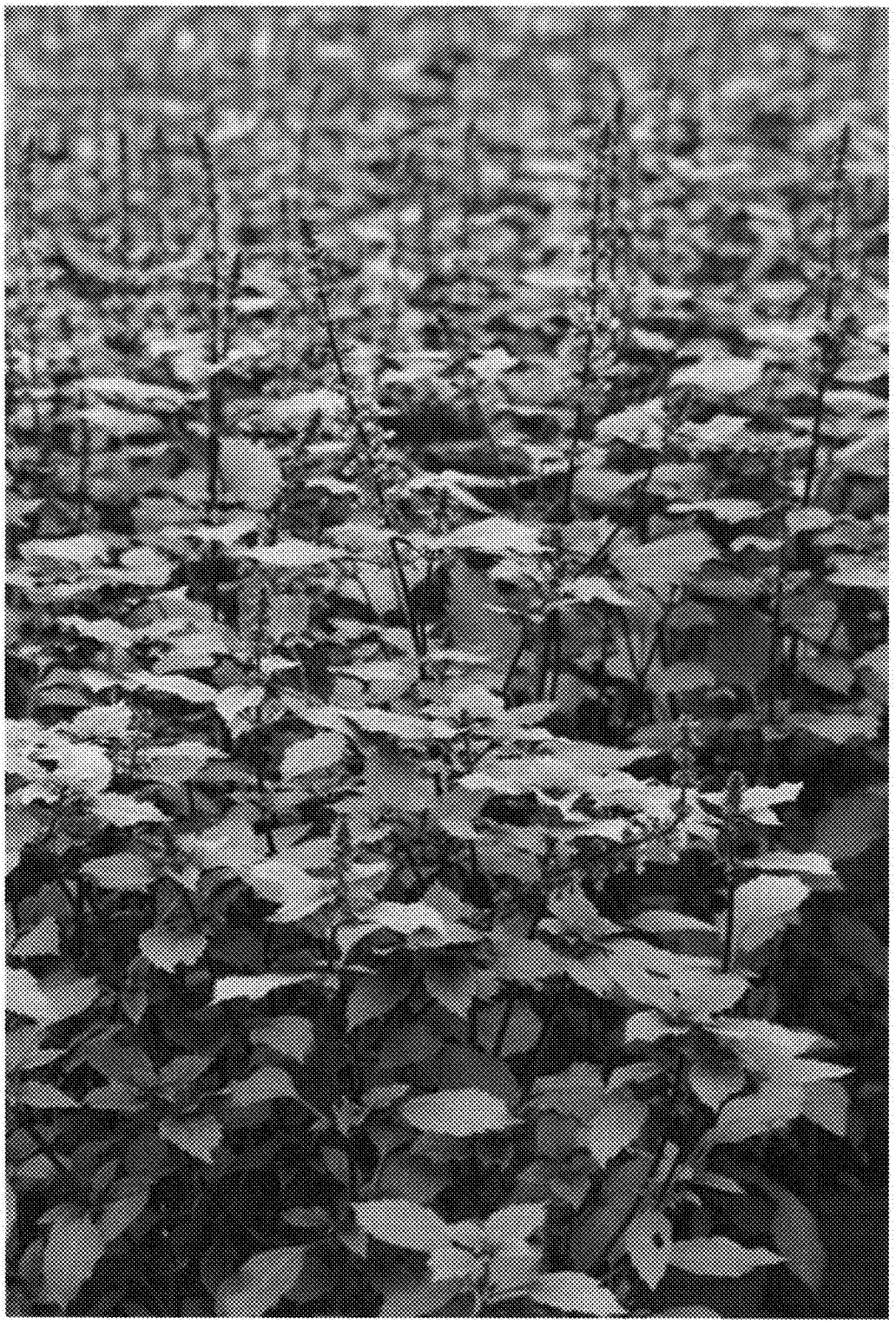
FIG. 3 is a photograph of the flowers and leaves of the new variety.
Figure 4:
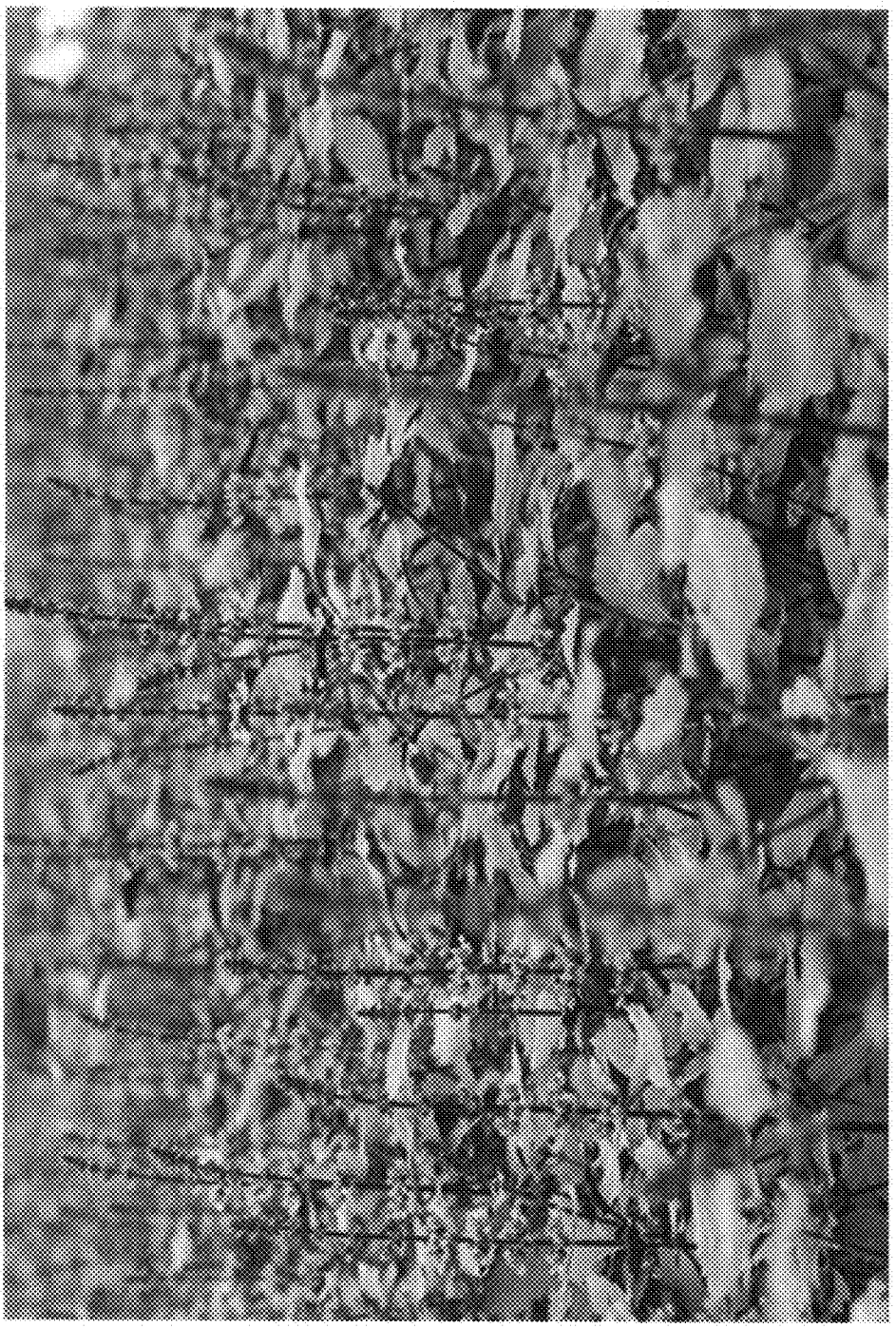
FIG. 4 is another photograph of the flowers and leaves of the new variety.
Figure 5:
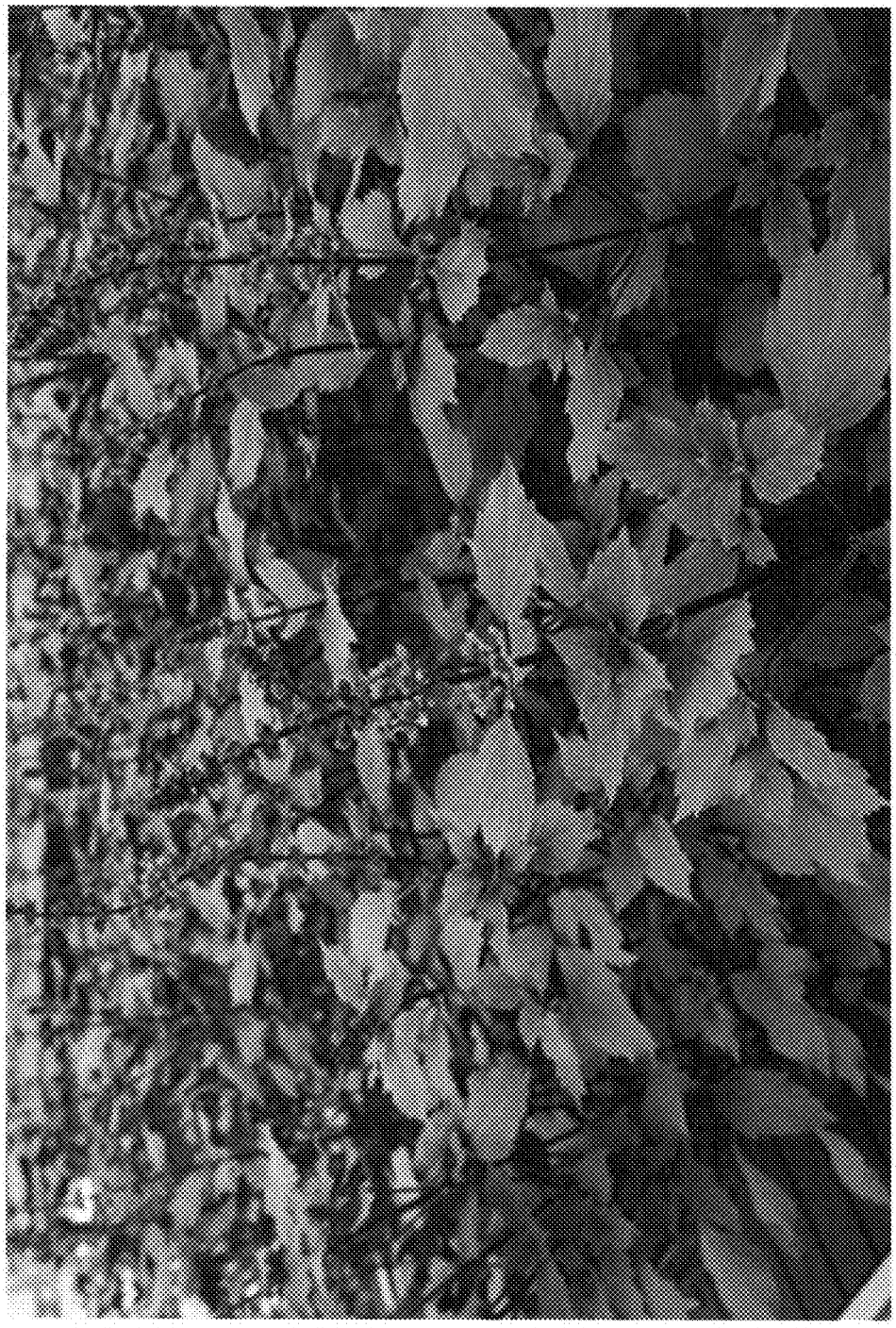
FIG. 5 is another photograph of the flowers and leaves of the new variety.
Figure 6:
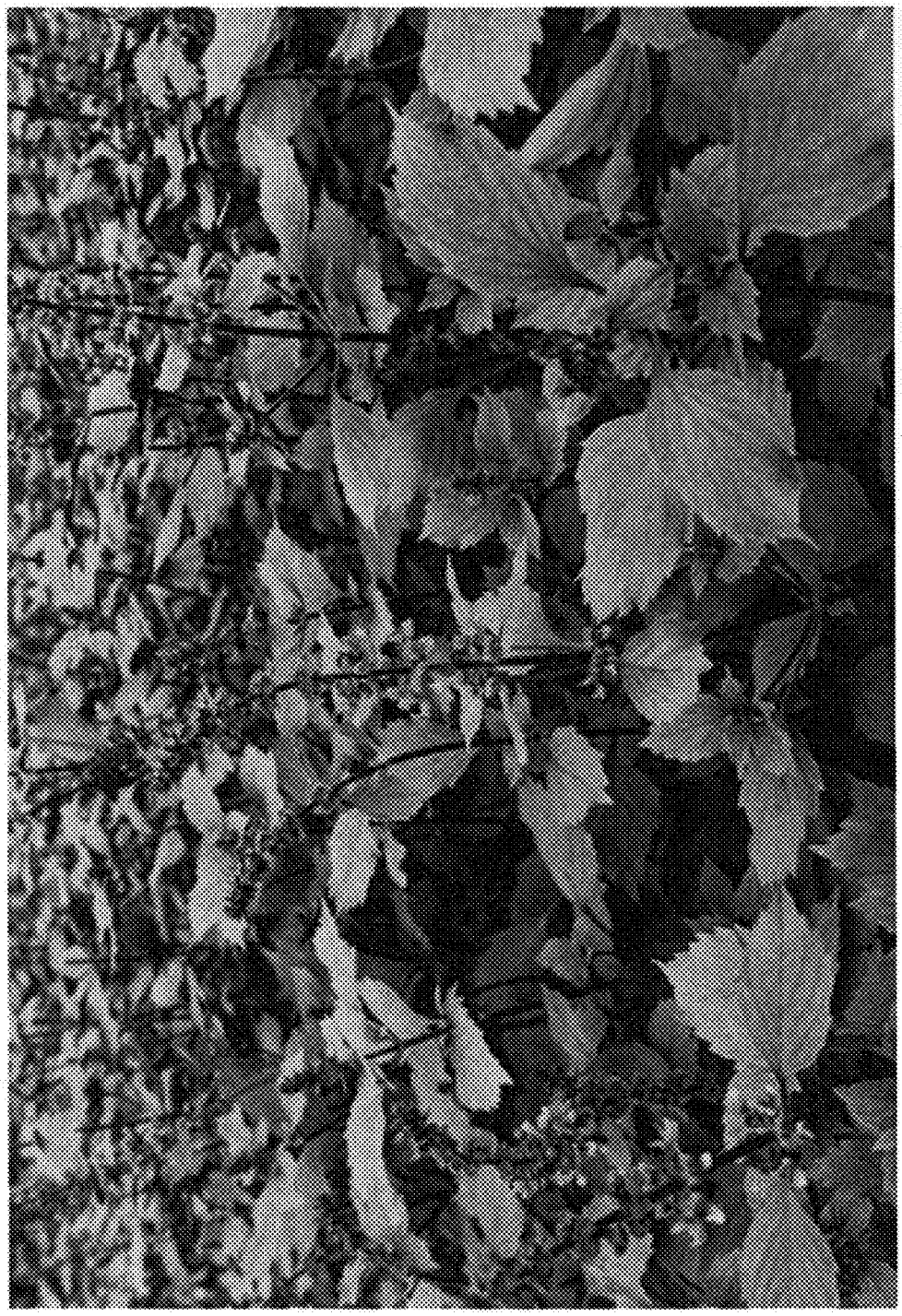
FIG. 6 is another photograph of the flowers and leaves of the new variety.
Figure 7:
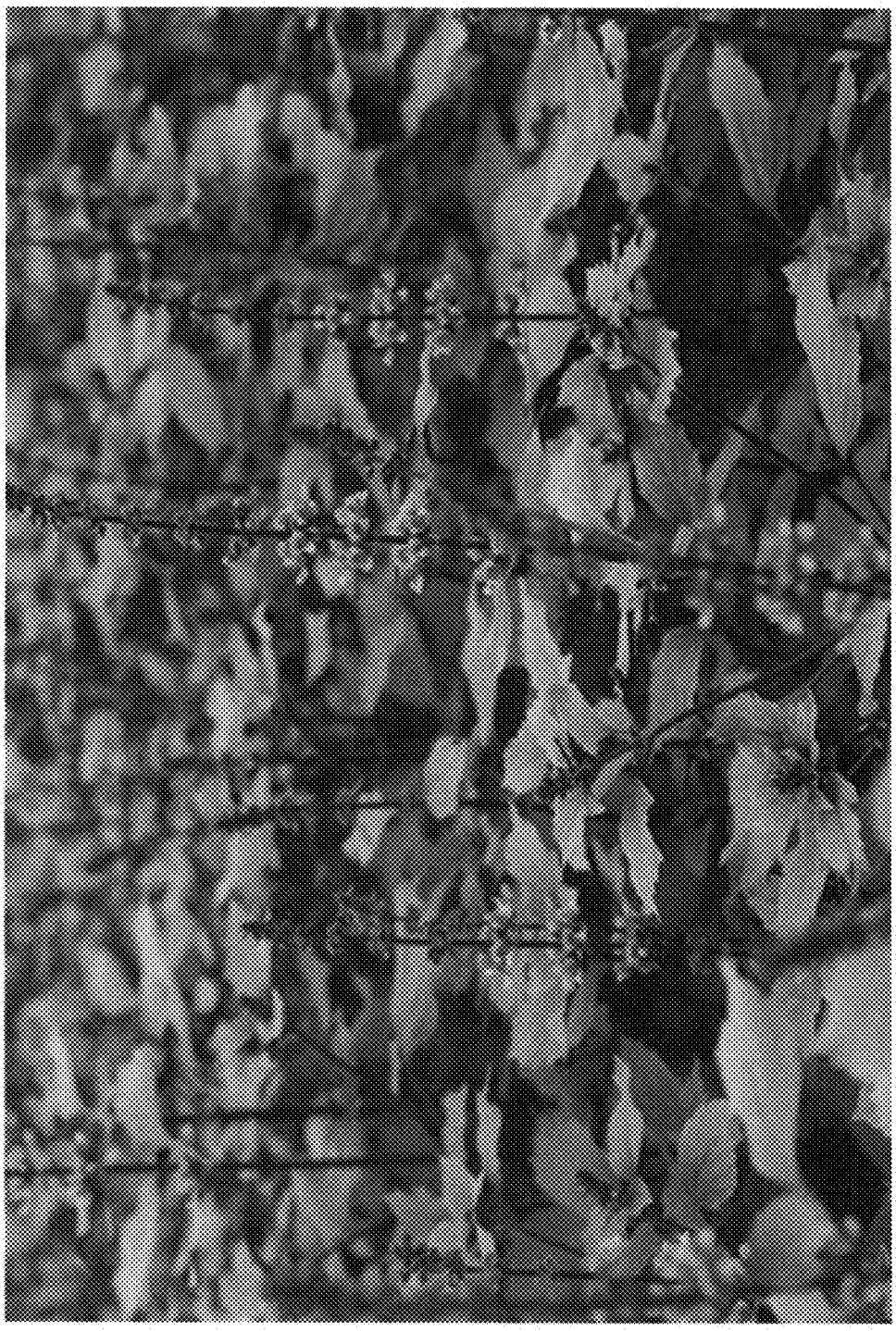
FIG. 7 is another photograph of the flowers and leaves of the new variety.
Figure 8:
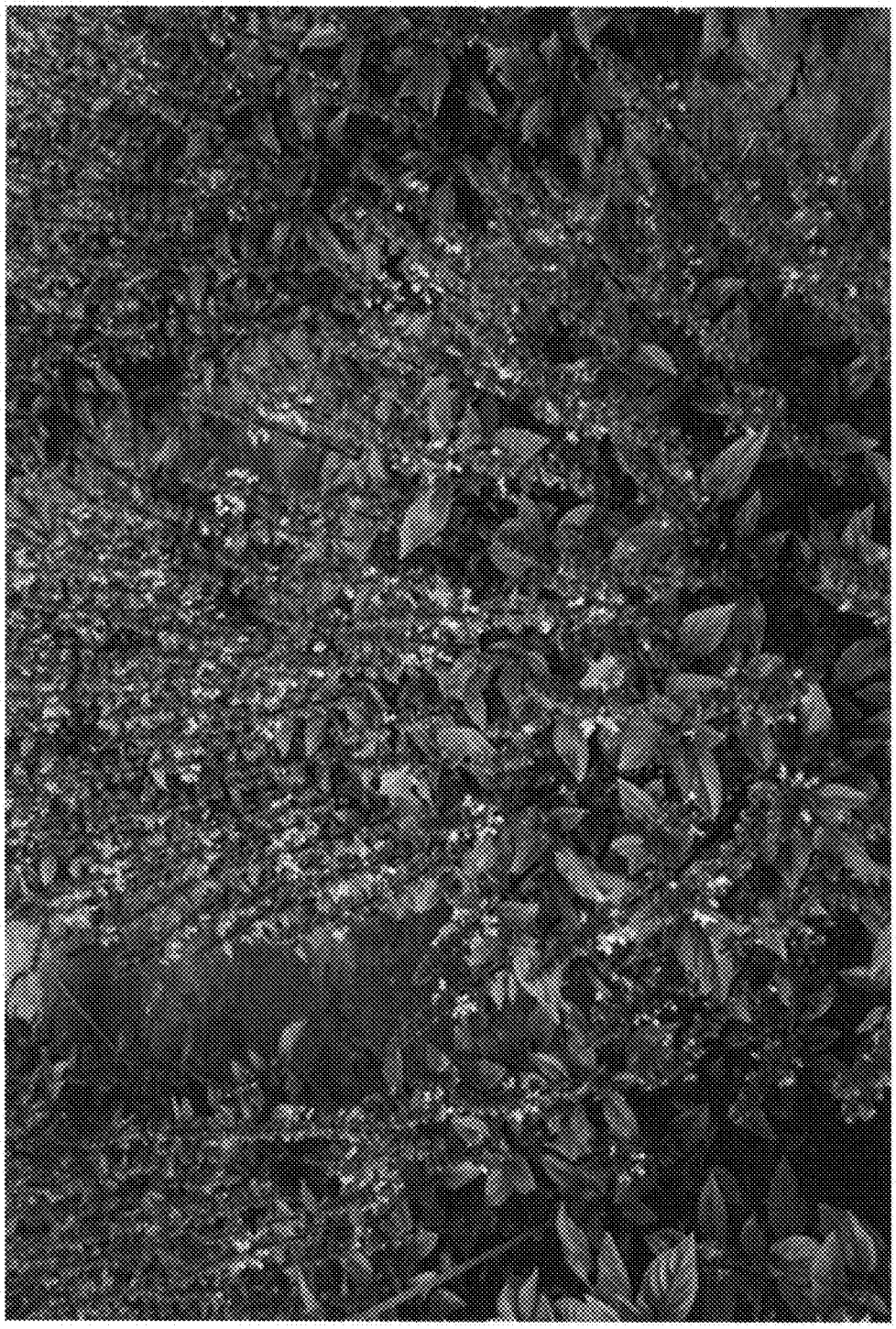
FIG. 8 is another photograph of the flowers and leaves of the new variety.
Figure 9:
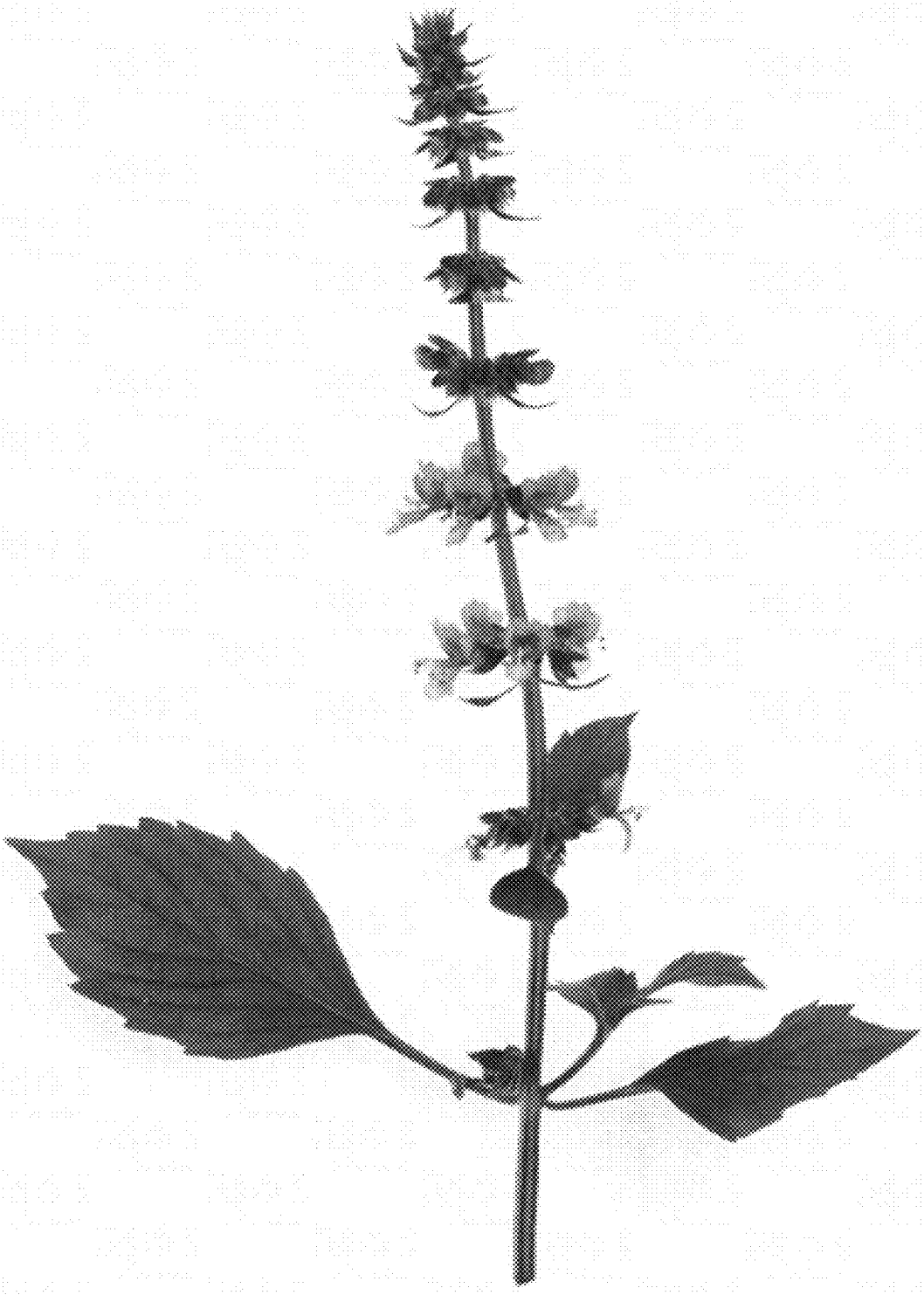
FIG. 9 is a photograph of a detached stem of the new variety.
Figure 10:
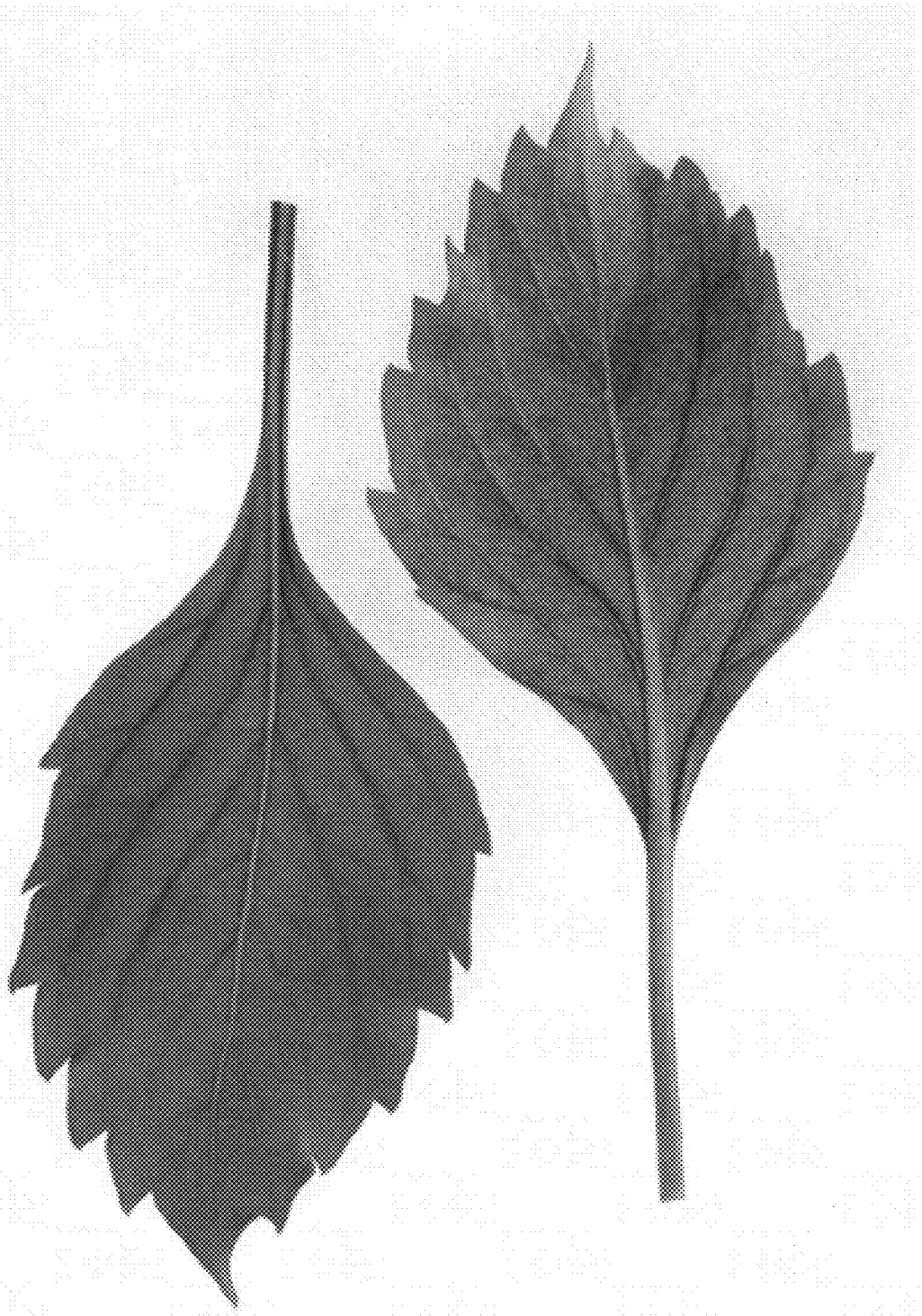
FIG. 10 is a close-up photograph of the upper and lower leaf surfaces of the new variety.
Figure 11:
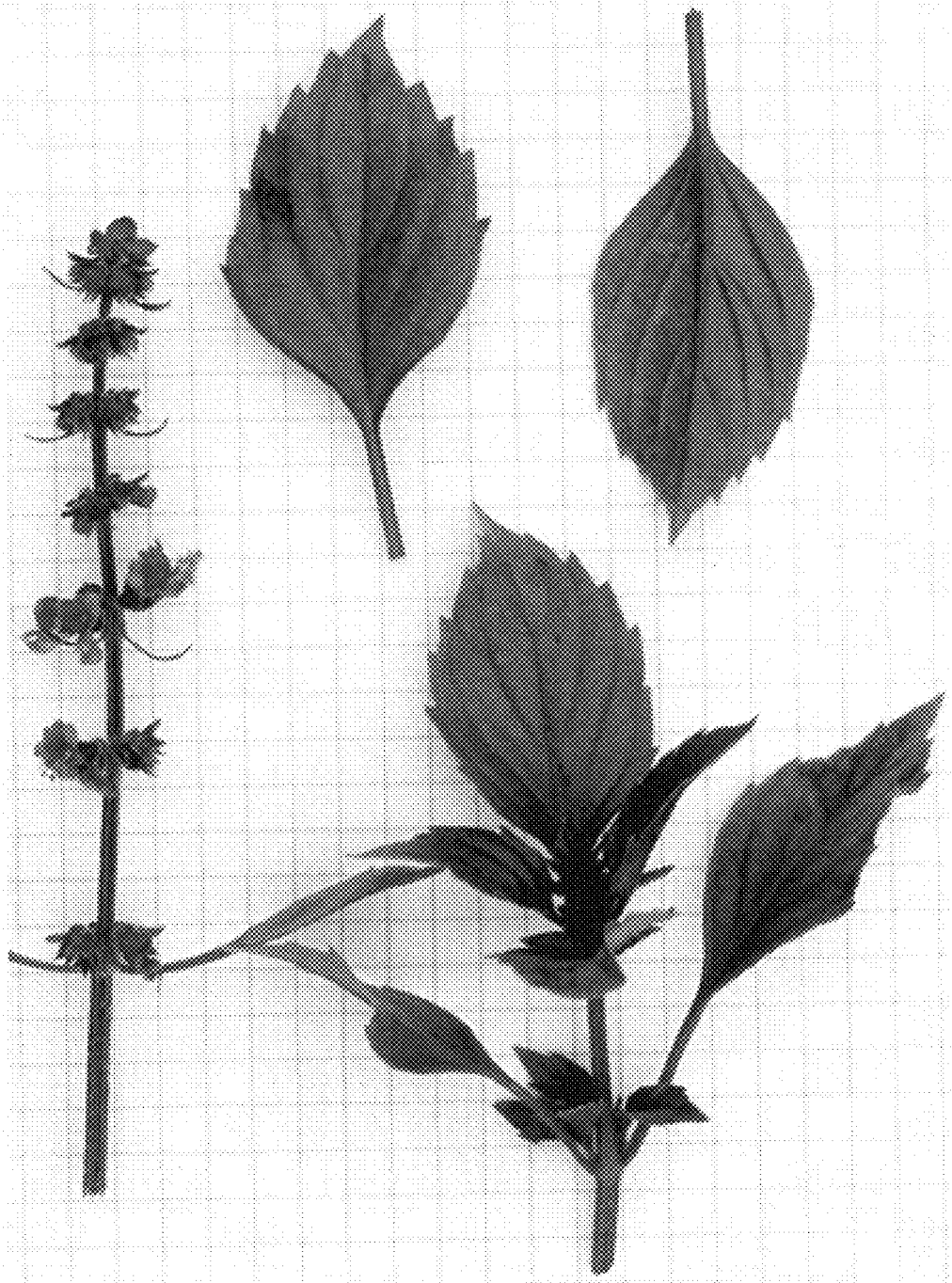
FIG. 11 is a photograph of detached leaves and flowers of the new variety.

Time to initiate roots: 5 days at 22° C.

Time to produce a rooted plant: 9 days at 22° C.

Root description: Finely branched white roots with a fibrous habit.

Form: Rounded.

Height from soil to top of plant: 60 cm.

Plant diameter: 50 cm.

Growth habit: Conglobate and round with a well-branched habit.

*Vigor*.—Medium, when compared to 'Habana' (U.S. Plant patent application Ser. No. 13/385,806) and 'Green Ball' (U.S. Plant patent application Ser. No. 13/385,809).

Main stem:

*Length*.—60 cm.

*Width*.—0.5 cm.

*Color*.—Purple Group RHS N77D to Violet Group RHS 83A.

*Number of branches*.—15-25.

*Node spacing*.—3-5 cm.

Leaves:

*Arrangement*.—Decussate; pinnate.

*Number of leaves per plant*.—Approximately 250.

*Length*.—6 cm.

*Width*.—4 cm.

*Shape of leaf (generally)*.—Elliptic.

*Shape of apex*.—Apiculate.

*Shape of base*.—Elliptic.

*Texture*.—No pubescence present. The veins are very distinct and visible because their color is more similar to the color of the stem and petiole, which contrasts with the main color of the leaf.

*Aspect*.—Horizontal.

*Margin type*.—Deep serration present.

*Upper surface color*.—Main color is Green Group 137A, with Purple Group RHS 77A in the center extending from the veins.

*Lower surface color*.—Main color is Green Group 137A, with Purple Group RHS 77A in the center extending from the veins.

*Veins*.—Upper surface description and color: Purple Group RHS N77B. Lower surface description and color: Purple Group RHS N77B.

*Petiole*.—Length: 4-6 cm. Diameter: 2 mm. Color: Purple-Violet Group RHS N80D to Violet Group RHS 83A. Texture: Hairy. Shape: Round.

Reproductive organs: 1 pistil and 4 stamens present.

Flowers:

*Natural flowering season*.—June through September in the Brandenburg Region of Germany.

*Number of flowers per plant*.—Approximately 800.

*Fragrance*.—Aromatic.

*Longevity*.—6-8 weeks.

*Flower type*.—Labiate.

*Flower height*.—0.5 cm.

*Flower diameter*.—0.3 cm.

*Petal color*.—Upper surface: Purple-Violet Group RHS N80D. Lower surface: Purple-Violet Group RHS N80D to Purple Group RHS 77A.

Seed description: Sterile.

Disease/pest resistance: Resistant to *Fusarium oxysporum*.

Weather tolerance: Very tolerant to rain and cold nights (down to 8° C.).

Harvesting season: Early summer to fall outdoors; year round indoors.

Flavor: Aromatic-spicy.

Aroma: Condimental.

Essential oils: Linalool-Methyl chavicol-type.

Productivity/yield per acre:

*Fresh*.—11 tons per acre.

*Dried*.—1.4 tons per acre.

Average life span: 5 months.

Use: Multiple uses. The new variety can be used as a pot plant, ornamental plant, culinary herb, or fresh and dried herb.

Fresh shelf life: Over 1 week under cool conditions (5-8° C.).

I claim:

1. A new and distinct variety of basil plant named 'Wild Magic' as herein described and illustrated.

* * * * *

UNITED STATES PATENT AND TRADEMARK OFFICE

CERTIFICATE OF CORRECTION

PATENT NO. : PP24,614 P3
APPLICATION NO. : 13/385805
DATED : July 8, 2014
INVENTOR(S) : Udo Schäfer It is certified that error appears in the above-identified patent and that said Letters Patent is hereby corrected as shown below:

On the Title Page, above "Botanical classification"
insert -- CROSS REFERENCE TO RELATED APPLICATIONS
The new variety was discovered in the same cultivated area as basil plants named 'Ajaka', 'Dark Lady', and 'Green Fortune', each respectively claimed in U.S. Plant Patent Application Nos. 13/385,808, 13/385,798, and 13/385,811. --

In the Specification
Column 4, Line 39, delete "/yield" and insert -- /Yield --

Signed and Sealed this
Fourteenth Day of October, 2014

Michelle K. Lee

Michelle K. Lee
*Deputy Director of the United States Patent and Trademark Office*